(12) United States Patent
Chelnokov

(10) Patent No.: US 12,097,067 B2
(45) Date of Patent: Sep. 24, 2024

(54) AUTOMATIC DETERMINATION OF TRANSFER FUNCTION FOR CT RECONSTRUCTION

(71) Applicant: James R. Glidewell Dental Ceramics, Inc., Newport Beach, CA (US)

(72) Inventor: Fedor Chelnokov, Khimki (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 209 days.

(21) Appl. No.: 17/588,918

(22) Filed: Jan. 31, 2022

(65) Prior Publication Data
US 2023/0240639 A1    Aug. 3, 2023

(51) Int. Cl.
| | |
|---|---|
| *G01T 1/29* | (2006.01) |
| *A61B 6/03* | (2006.01) |
| *A61B 6/42* | (2024.01) |
| *A61B 6/58* | (2024.01) |

(52) U.S. Cl.
CPC ............ *A61B 6/582* (2013.01); *A61B 6/032* (2013.01); *A61B 6/4241* (2013.01)

(58) Field of Classification Search
None
See application file for complete search history.

(56) References Cited

U.S. PATENT DOCUMENTS

| | | | |
|---|---|---|---|
| 5,375,156 A | 12/1994 | Kuo-Petravic et al. | |
| 2008/0312884 A1* | 12/2008 | Hostettler | G06T 5/50 |
| | | | 703/2 |
| 2009/0103793 A1* | 4/2009 | Borland | G06T 15/08 |
| | | | 382/131 |
| 2013/0202166 A1* | 8/2013 | Koehler | G06T 11/006 |
| | | | 382/128 |
| 2018/0132982 A1 | 5/2018 | Nikolskiy et al. | |
| 2018/0153796 A1* | 6/2018 | Lin | A61K 31/405 |
| 2020/0158663 A1* | 5/2020 | Danielsson | G01T 1/247 |
| 2020/0330059 A1* | 10/2020 | Fredenberg | A61B 6/4291 |

OTHER PUBLICATIONS

C.L. Lawson et al., Nonlinear Models, Modeling of Data, Chapter 15, pp. 681-689.
Maria E. Lyra et al., Filtering in SPECT image reconstruction, ResearchGate, International Journal of Biomedical Imaging, Jun. 2011, Department of Radiology, Radiation Physics Unit, University of Athens, in 15 pages.
Avinash C. Kak et al., Principles of Tomographic Imaging, Electronic Copy 1999 by A.C. Kak et al., Institute of Electrical and Electronics Engineers, Inc. New York, in 333 pages.
Devin Held, The University of Western Ontario, Analysis of 3D Cone-Beam CT Image Reconstruction Performance on a FPGA, 2016, Western Graduate & Postdoctoral Studies, Dec. 16, 2016, 12:00am, in 75 pages.

(Continued)

*Primary Examiner* — Marcus H Taningco
(74) *Attorney, Agent, or Firm* — Klarquist Sparkman, LLP

(57) ABSTRACT

A computer-implemented method of automatically determining photon-count to penetrated depth function for a CT reconstruction includes performing one or more test CT reconstructions on one or more radiographs, each test CT reconstruction using a test transfer function, to provide one more test reconstructions and determining a final transfer function from the one or more test reconstructions.

20 Claims, 16 Drawing Sheets performing one or more test CT reconstructions on one or more radiographs, each test CT reconstruction using a test transfer function, to provide one more test reconstructions — 1402 determining a final transfer function from the one or more test reconstructions — 1404

(56) References Cited

OTHER PUBLICATIONS

David Walter et al., Photon Counting and Energy Discriminating X-Ray Detectors- Benefits and Applications, 19th World Conference on Non-Testing 2016, in pages.

Graham Davis et al., A Modeling Approach to Beam Hardening Correction, Development in X-Ray Tomography VI, edited by Stuart R. Stock, vol. 7078, 70781E, (2008), SPIE Digital Library, in 11 pages.

* cited by examiner

528

AUTOMATIC DETERMINATION OF TRANSFER FUNCTION FOR CT RECONSTRUCTION

BACKGROUND

A computed tomography scan ("CT scan") typically involves placing a physical object on a rotating platform inside a CT scanner between an x-ray source and x-ray detector and rotating the object around an axis of rotation to generate radiographs from the x-rays detected by the detector. CT scanning thus produces radiographs with every pixel (x,y) containing the number I(x,y) of x-ray photons registered at the pixel (i.e. photons not absorbed by the scanned object).

Conventionally, the radiographs can be tomographically reconstructed into a 3D representation of the object scanned ("CT reconstruction"). One example of CT reconstruction can be found in, for example, in the publication *Principles of Computerized Tomographic Imaging* (A. C. Kak and Malcolm Slaney, *Principles of Computerized Tomographic Imaging*, IEEE Press, 1988), the entirety of which is incorporated by reference herein. Other types of CT reconstruction can also be performed.

CT reconstruction typically requires a total attenuation coefficient t(x,y) for every pixel of the radiograph, which in the case of single-material object can proportional to the length of the path the x-ray travelled through the object. Conventional techniques for determining the total attenuation coefficient typically assume a theoretical relationship between detector readings and the attenuation coefficients. This can produce undesirable artifacts in the 3D representation of the object scanned, particularly for scanned objects made of different materials. Additionally, due to variability in the scanned object shape, making precise measurements of various path lengths can be challenging. Finally, due to the number of different potential materials in the scanned object, developing a calibration object of simple shape for every single material can be challenging.

SUMMARY

Disclosed is a computer-implemented method of automatically determining photon-count to penetrated depth function for a CT reconstruction. The method includes performing one or more test CT reconstructions on one or more radiographs, each test CT reconstruction using a test transfer function, to provide one more test reconstructions and determining a final transfer function from the one or more test reconstructions.

Disclosed is a system to automatically determine a photon-count to penetrated depth function for a CT reconstruction, the system including: a processor and a non-transitory computer-readable storage medium comprising instructions executable by the processor to perform steps including: performing one or more test CT reconstructions on one or more radiographs, each test CT reconstruction using a test transfer function, to provide one more test reconstructions; and determining a final transfer function from the one or more test reconstructions.

Disclosed is a non-transitory computer readable medium storing executable computer program instructions to automatically determine a photon-count to penetrated depth function for a CT reconstruction, the computer program instructions including instructions for: performing one or more test CT reconstructions on one or more radiographs, each test CT reconstruction using a test transfer function, to provide one more test reconstructions; and determining a final transfer function from the one or more test reconstructions.

DETAILED DESCRIPTION

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Additionally, the description sometimes uses terms like "provide" or "achieve" to describe the disclosed methods. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Figure 1:
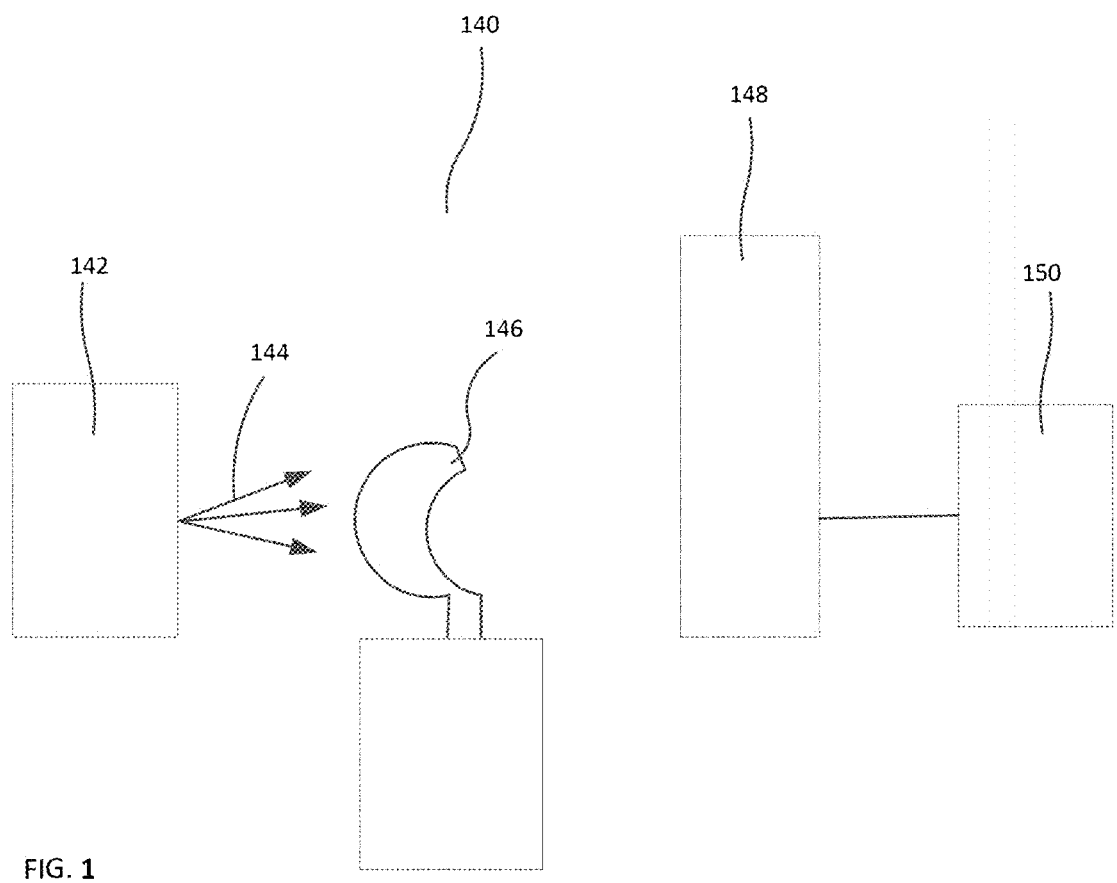
FIG. 1 is a schematic diagram of a computed tomography (CT) scanning system in some embodiments.

In one embodiment of the present disclosure, a computed tomography (CT) scanner uses x-rays to make a detailed image of an object. A plurality of such images are then combined to form a 3D model of the object. A schematic diagram of an example of a CT scanning system 140 is shown in FIG. 1. The CT scanning system 140 includes a source of x-ray radiation 142 that emits an x-ray beam 144. An object 146 being scanned is placed between the source 142 and an x-ray detector 148. In some embodiments, the object can be, for example, a triple-tray physical dental impression or any other type of physical dental impression. In some embodiments, for example, any other type of physical dental impression can be scanned. In some embodiments, the object can be any object that can, for example, fit in a CT scanning system and be penetrated by x-rays. The x-ray detector 148, in turn, is connected to a processing system 150 that is configured to receive the information from the detector 148 and to convert the information into a radiograph. Those skilled in the art will recognize that the processing system 150 may comprise one or more processors and/or computers that may be directly connected to the detector, wirelessly connected, connected via a network, or otherwise in direct or indirect communication with the detector 148 and/or with the CT scanning system 140.

An example of a suitable scanning system 140 includes a Nikon Model XTH 255 CT Scanner (Metrology) which is commercially available from Nikon Corporation. The example scanning system includes a 225 kV microfocus x-ray source with a 3 µm focal spot size to provide high performance image acquisition and volume processing. The processing system 150 may include a storage medium that is configured with instructions to manage the data collected by the scanning system. A particular scanning system is described for illustrative purposes; any type/brand of CT scanning system can be utilized.

Figure 2:
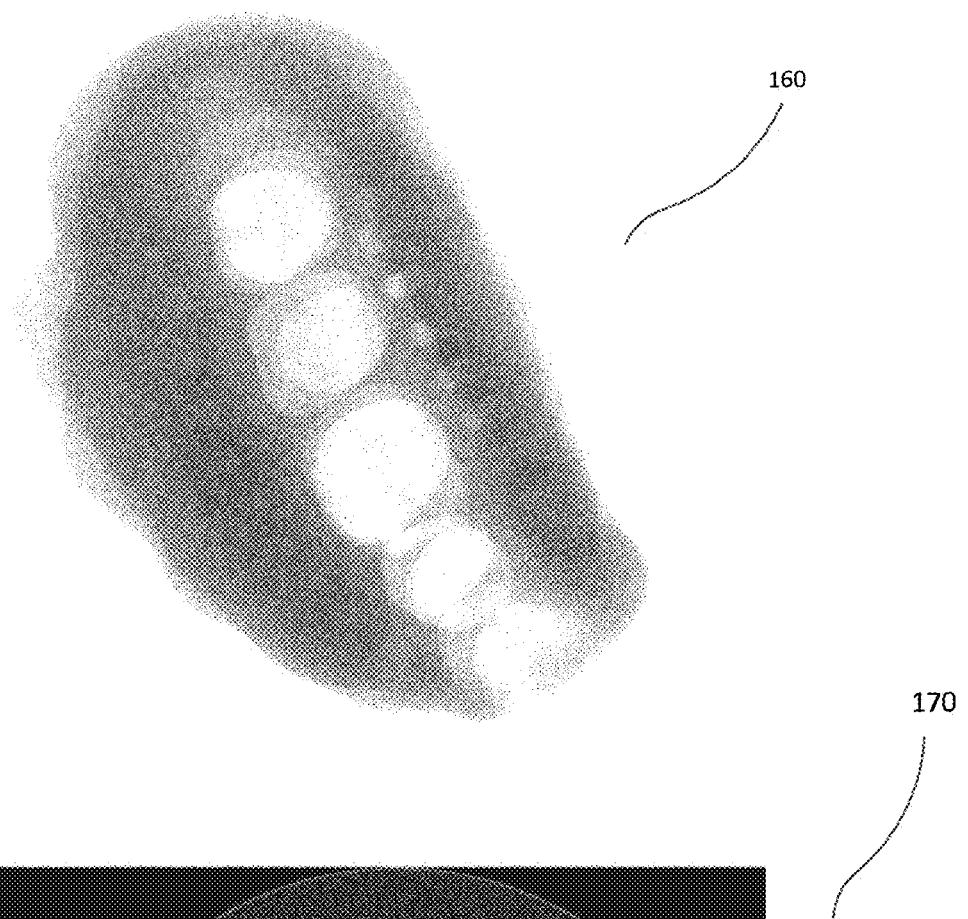
FIG. 2 is a 2-dimensional (2D) radiographic image of a dental impression tray containing a dental impression in some embodiments.

One example of CT scanning is described in U.S. Patent Application No. US20180132982A1 to Nikolskiy et al., which is hereby incorporated in its entirety by reference. As noted above, during operation of the scanning system 140, the object 146 is located between the x-ray source 142 and the x-ray detector 148. A series of images of the object 146 are collected by the processing system 150 as the object 146 is rotated in place between the source 142 and the detector 146. An example of a single radiograph 160 is shown in FIG. 2. The radiograph 160 and all radiographs described herein are understood to be digital. In one embodiment, a series of 720 images are collected as the object 146 is rotated in place between the source 142 and the detector 148. In other embodiments, more images or fewer images may be collected as will be understood by those skilled in the art.

Figure 3:
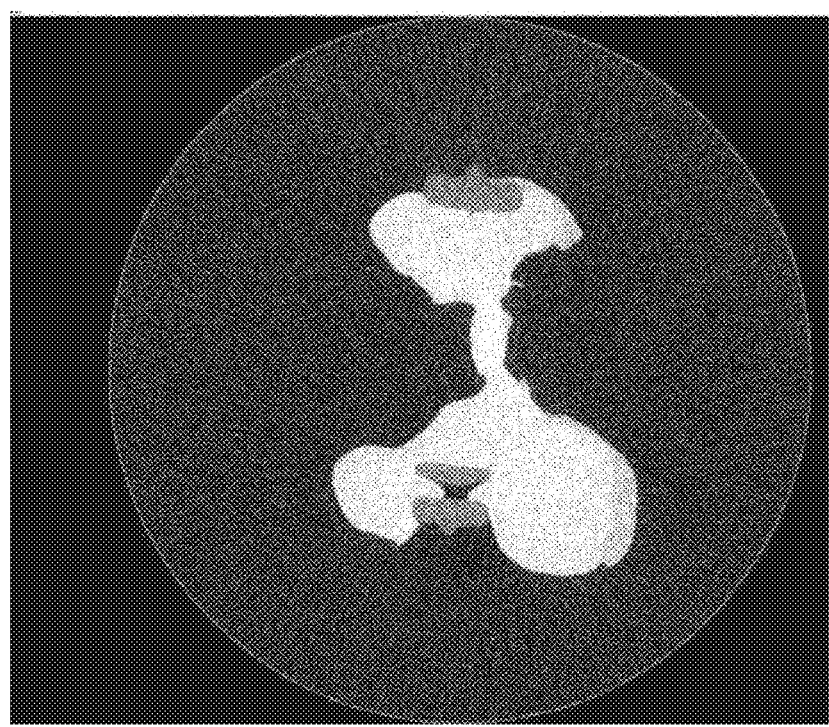
FIG. 3 is a cross-section of a 3-dimensional (3D) volumetric image in some embodiments.

Conventionally, the plurality of radiographs 160 of the object 146 are generated by and stored within a storage medium contained within the processing system 150 of the scanning system 140, where they may be used by software contained within the processor to perform additional operations. For example, in an embodiment, the plurality of radiographs 160 can undergo tomographic reconstruction in order to generate a 3D virtual image 170 (see FIG. 3) from the plurality of 2D radiographs 160 generated by the scanning system 140. In the embodiment shown in FIG. 3, the 3D virtual image 170 is in the form of a volumetric image or volumetric density file (shown in cross-section in FIG. 3) that is generated from the plurality of radiographs 160 by way of a CT reconstruction algorithm associated with the scanning system 140.

Figure 4:
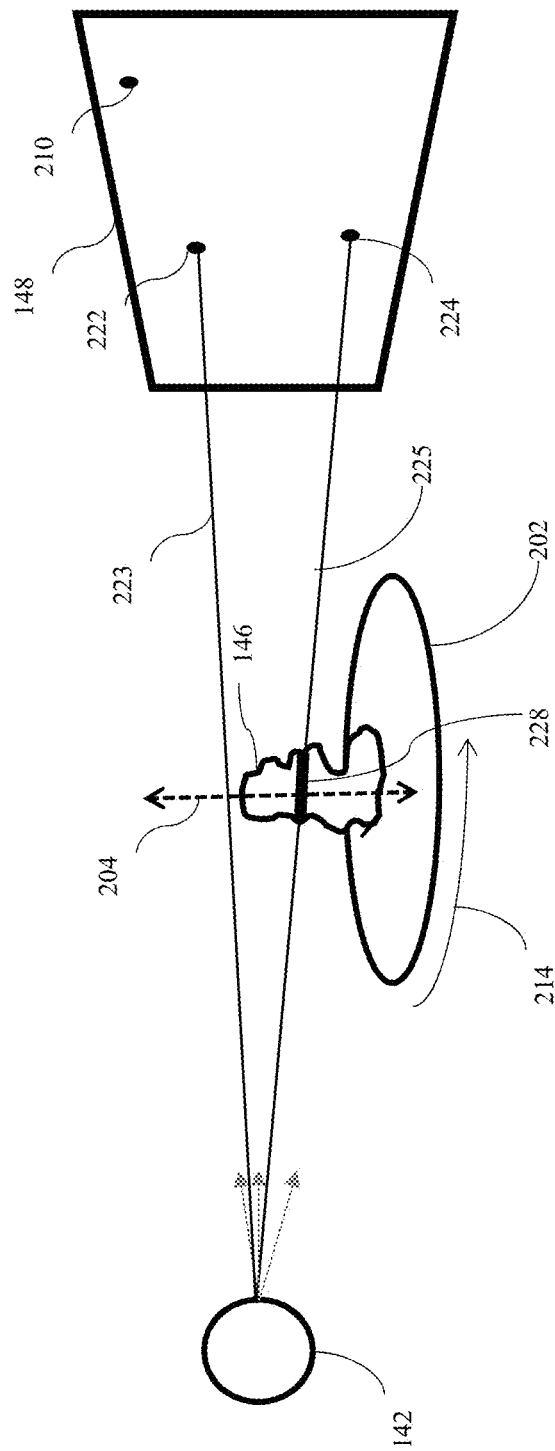
FIG. 4 is a schematic diagram of portions of a CT scanning system in some embodiments.

FIG. 4 is an illustration of portions of a CT scanning system as discussed previously. Certain features of the CT scanning system are not shown for clarity. Other conventional CT scanning systems known in the art can also be utilized. Conventionally, the physical object 146 to be scanned is placed inside the CT scanner on a rotational platform 202 between an x-ray source 142 and x-ray detector 148. The physical object 146 is exposed to x-rays generated by the x-ray source 142 that travel from the x-ray source 142 through the physical object 146 and to the x-ray detector 148. The x-ray detector 148 conventionally includes a detector pixel array (row of detector pixels and column of detector pixels) which detects any incident x-rays to generate a radiograph, for example. In some embodiments, the x-ray detector 148 can include an array resolution of 1,000×1,000 pixels, for example. In some embodiments, the number of pixels can be at least 1 million pixels, for example. Other numbers of pixels can also be present. Other array resolutions are also possible. Conventionally, as the physical object 146 is rotated around an axis of rotation 204, the x-ray detector 148 detects x-rays incident on each pixel such as detector pixel 210 (and any other detector pixels) at each rotational position to generate multiple radiographs. The x-ray detector 148 can detect a photon count at each pixel for each radiograph generated at each rotational position. In some embodiments, the possible photon count can be any value. In some embodiments, the possible photon count range can be anywhere from 0 to 65535 photons per pixel, for example. Other photon count ranges per pixel are also possible. In some embodiments, the physical object 146 can be rotated 360 degrees once, and a direction of rotation 214 can be either clockwise or counterclockwise. For example, detector pixel 222 can experience the maximum photon count, $I_0$ in some embodiments since ray 223 that does not pass through the object 146. In another example, detector pixel 224 can experience a lesser than maximum photon count, I in some embodiments since ray 225 penetrates through the object 146. The number of photons detected at detector pixel 224 can be based on a length path 228 the ray travels through the object 146.

Conventional/standard CT scanning systems allow setting the total number of radiographs desired prior to scanning. Conventionally, the x-ray detector 148 detects and acquires a radiograph every rotational degree based on the total number of radiographs desired. For example, the rotational degree can conventionally be determined as follows by the standard CT scanner: 360 degrees divided by the total number of radiographs, for example. In some embodiments, the total number of radiographs can be at least 500 radiographs, for example. The x-ray detector 148 conventionally detects and acquires the radiograph as well as the photon count for every detector pixel such as detector pixel 210. An example of conventional photon counting and x-ray detectors can be found, for example, in *Photon Counting and Energy Discriminating X-Ray Detectors—Benefits and Applications* (David WALTER, Uwe ZSCHERPEL, Uwe EWERT, BAM Bundesanstalt für Materialforschung und-prüfung, Berlin, Germany, 19$^{th}$ World Conference on Non-Destructive Testing, 2016), the entirety of which is incorporated by reference herein. In some embodiments, the x-ray detector 148 can store the acquired radiographs. The axis of rotation 204 may not be visible, and is the axis around which the object rotates.

A single CT scan can therefore generate multiple radiographs in some embodiments in a single CT scan. CT scanning thus produces radiographs with every pixel (x,y) of a radiograph containing the number I(x,y) of x-ray photons registered at the pixel (i.e. photons not absorbed by the scanned object).

Figure 5A:
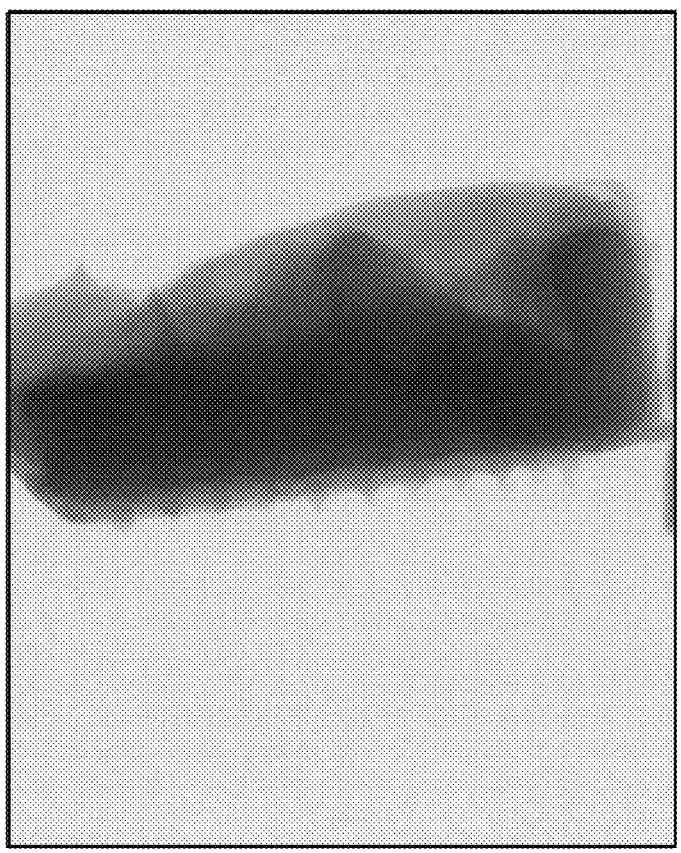
FIGS. 5(a), 5(b), and 5(c) illustrate examples of radiographs in some embodiments for example.
Figure 5B:
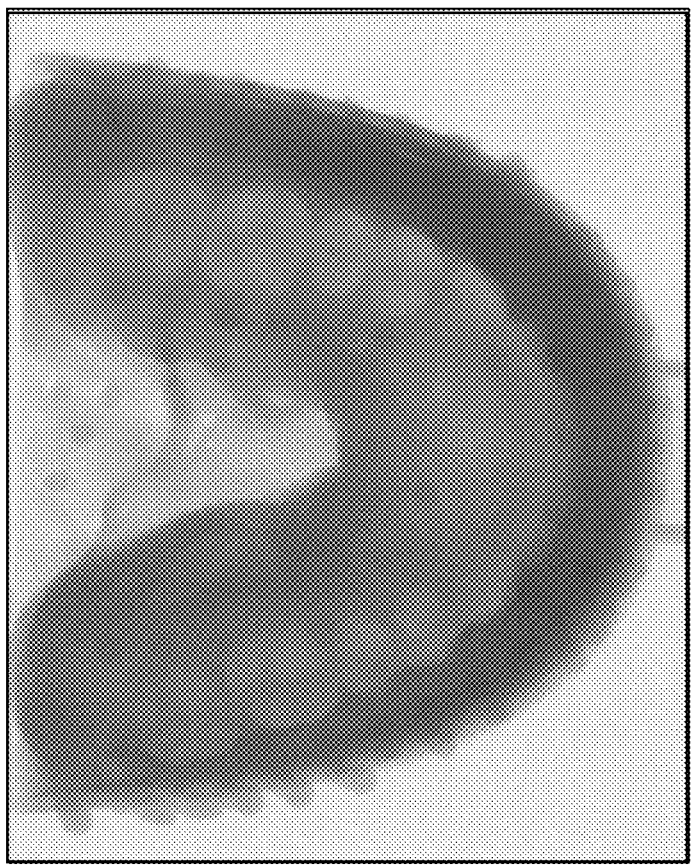
Figure 5C:

FIGS. 5(a)-5(c) illustrate examples of a first radiograph 524, a second radiograph 526, and a third radiograph 528, respectively, of the multiple radiographs. Three radiographs are shown for illustration purposes only; the plurality of radiographs can include any number of radiographs, such as at least 500 radiographs, for example, in some embodiments. The first radiograph 524 can be the first radiograph pixels detected at a first rotational position, the second radiograph 526 can be the second radiograph pixels detected at a second rotational position, and the third radiograph 528 can be the third radiograph pixels detected at a third rotational position, for example. The nth radiograph can be the nth radiograph pixels detected at a nth rotational position as the physical object 146 is rotated around the axis of rotation 204 from zero to a fixed number of degrees such as 360 degrees, in some embodiments, for example. The number of radiograph pixels shown is also for illustration purposes only, and can be greater or smaller in value. In some embodiments, there can be 1,000 rows×1,000 columns of pixels, for example.

Figure 6:
FIG. 6 illustrates an example of a slice of a CT reconstructed volume generated in some embodiments.

CT reconstruction typically requires a total attenuation coefficient t(x,y) for every pixel of the radiograph, which in the case of single-material object can be proportional to the length of the path the x-ray went through the object. However, CT scans can be of objects made of multiple materials. Conventional techniques for determining the total attenuation coefficient typically assume a theoretical relationship between detector readings and the attenuation coefficients. This can produce undesirable artifacts in the 3D representation of the object scanned, particularly for scanned objects made of different materials. FIG. 6 illustrates an example of a slice 600 of a CT reconstructed volume generated using conventional techniques. As can be seen, the slice 600 includes artifacts such as stokes 602 in empty regions and/or uneven density for different regions of the same object appearing in the slice such as object region 604 and object region 606. This can be caused by applying a theoretical transfer function, for example.

Some embodiments include a computer-implemented method of automatically determining photon-count to penetrated depth function for a CT reconstruction. In some embodiments, the photon-count to penetrated depth function can be referred to as a "transfer function".

In some embodiments, automatically determining photon-count to penetrated depth function for a CT reconstruction can include performing one or more test CT reconstructions on one or more radiographs, each test CT reconstruction using a different test transfer function, to provide one more test reconstructions. In some embodiments, the computer-implemented method receives the one or radiographs from a CT scan of an object. In some embodiments, the object can include one or more materials, each of the materials having a different material density. In some embodiments, the one or more radiographs can include radiograph(s) of a physical dental impression. In some embodiments, the physical dental impression can be any type of dental impression, including but not limited to a triple tray, full arch, double full arch, etc. In some embodiments, the physical impression can include one or more materials such as a main impression material, a second impression material, and material of a plastic handle, for example. Other materials can also be present in some embodiments. In some embodiments, the impression itself can be made of multiple materials.

In some embodiments, the one or more radiographs can include one or more down-sampled radiographs. In some embodiments, the computer-implemented method generates the one or more down-sampled radiographs. In some embodiments, the computer-implemented method can receive the one or more down-sampled radiographs. In some embodiments, the one or more down-sampled radiographs are generated prior to generating one or more test CT reconstructions. In some embodiments, the one or more down-sampled radiographs can be generated prior to performing the final CT reconstruction. The one or more down-sampled radiographs can reduce the amount of input data to allow more reconstructions during some time period compared to not down-sampled, full resolution mode.

In some embodiments, the one or more down-sampled radiographs can be generated by block sampling. In some embodiments, block sampling can include replacing a block of pixels (also known as "multi-pixel block") within each of the one or more radiographs with a single block representative pixel. The block of pixels can include two or more pixels, and down-sampling can provide a reduction of resolution of the radiograph. The block of pixels can include a square block of pixels within a radiograph in some embodiments, for example. In some embodiments, the block sampled radiograph can include a block representative pixel for each block of the original radiograph. In some embodiments, the block representative pixel can be a mean value of pixels in the block of pixels. In some embodiments, the block representative pixel can be an average of the value in the block of pixels. In some embodiments, the block representative pixel can be any value that combines or uses the values in the block of pixels. In some embodiments, down-sampling reduces a resolution of the one or more radiographs.

Figure 7:
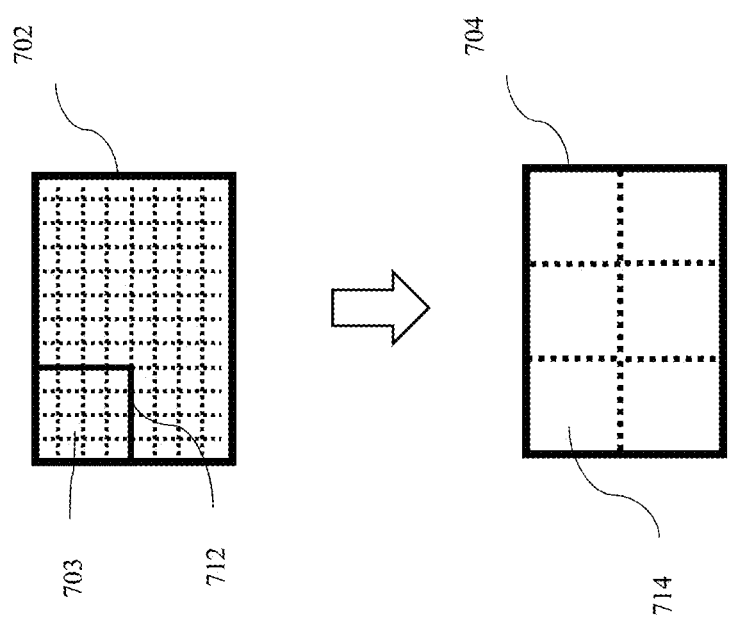
FIG. 7 shows an example of block sampling in some embodiments.

FIG. 7 illustrates an example of block sampling, where a radiograph 702 is block sampled to provide down-sampled radiograph 704. As illustrated in the example, a multi-pixel block 712 can include two or more pixels. Multi-pixel block 712 includes, for example, 4×4 pixels, including pixel 703. Block sampling can down sample the multi-pixel block 712 into a single block representative pixel 714, for example. In some embodiments, the representative pixel 714 can include a mean value of pixels in the multi-pixel block 712. In some embodiments, the representative pixel 712 can be an average of the value in the multi-pixel block 712. In some embodiments, the representative pixel 714 can be any value that combines or uses the values in the multi-pixel block 712. Additional multi-pixel blocks can be reduced to their respective single block representative pixels. In some embodiments, the entire radiograph 702 can be divided into several multi-pixel blocks, and each multi-pixel block sampled to provide its respective single block representative pixel in the down-sampled radiograph 704, for example. In the example, radiograph 702 is reduced by 16 times to provide block sampled radiograph 704. For example, radiograph 702 has a resolution of 96 pixels, and block sampled radiograph 704 has a resolution of 6 pixels. The number and arrangement of pixels in the example is for illustrative purposes only, and can vary.

In some embodiments, the one or more down-sampled radiographs can be generated by inter-radiograph down-sampling. In some embodiments, inter-radiograph down-sampling can include generating one or more down-sampled radiographs by selecting fewer than the total number of radiographs produced by a CT scan. In some embodiments, inter-radiograph down-sampling can include generating the one or more down-sampled radiographs by replacing one or more consecutive CT scanner radiographs with a single representative radiograph. In some embodiments, the single representative radiograph can include one or more positional representative pixels of each corresponding pixel position across one or more radiographs. In some embodiments, the positional representative pixel can be a mean value of pixels at a pixel position across one or more radiographs. In some embodiments, the positional representative pixel can be an average of pixels at a pixel position across one or more radiographs. In some embodiments, the positional representative pixel can be any value that combines or uses the values of pixels at a pixel position across one or more radiographs. In some embodiments, inter-radiograph down-sampling reduces a resolution of the one or more radiographs.

Figure 8:
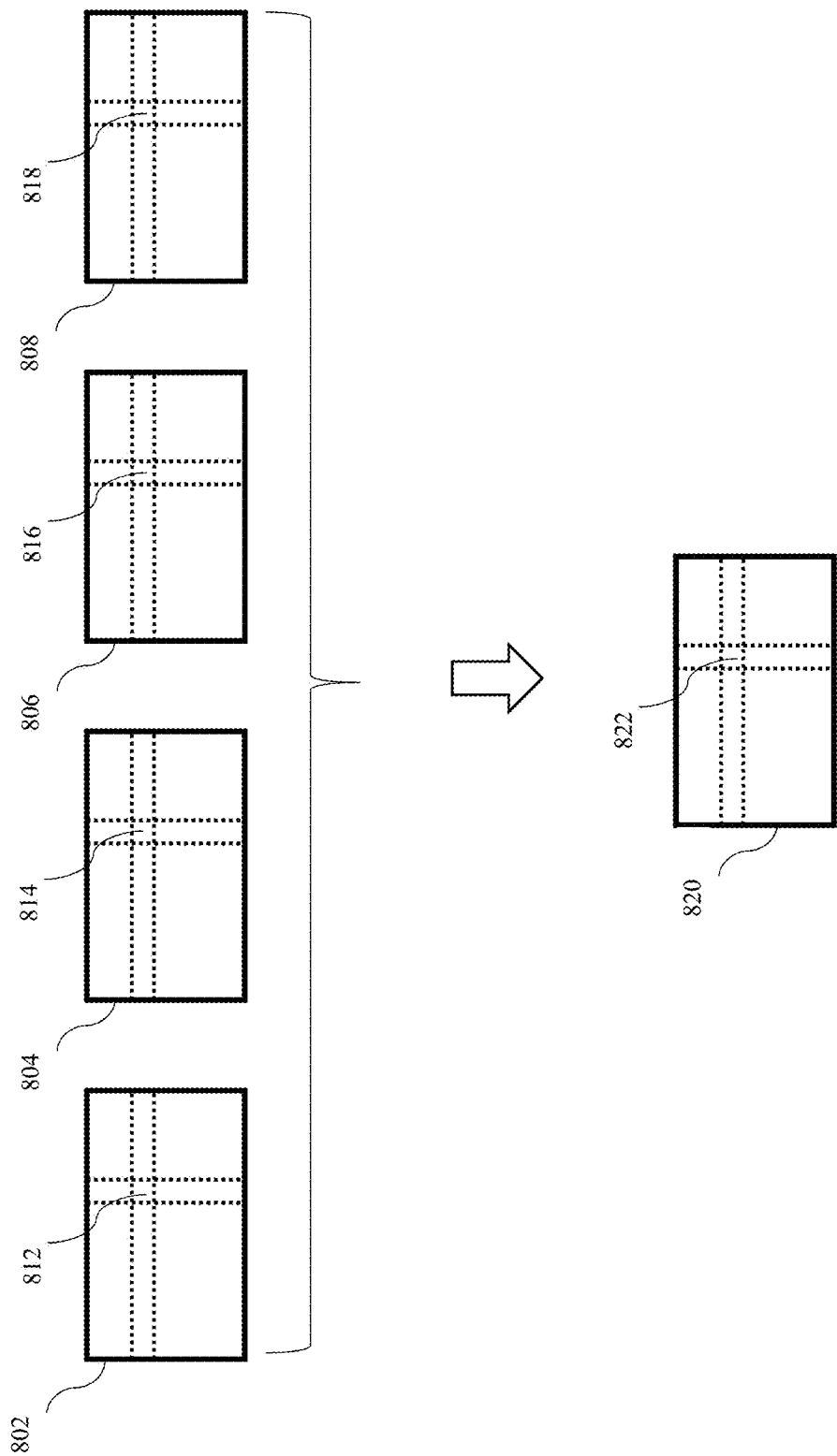
FIG. 8 illustrates one example of inter-radiograph down-sampling to generate down-sampled radiographs in some embodiments.

FIG. 8 illustrates one example of inter-radiograph down-sampling to generate down-sampled radiographs by replacing one or more consecutive CT scanner radiographs with a single representative radiograph. The figure illustrates four consecutive radiographs from a CT scan: first radiograph 802, second radiograph 804, third radiograph 806, and fourth radiograph 808. Four radiographs are shown for illustrative purposes only. More or fewer radiographs can be used. The computer-implemented method can down-sample the consecutive radiographs by generating a positional representative pixel for each pixel position across the consecutive radiographs. For example, the first radiograph 802 can include a first radiograph pixel 812 at an x,y position in the first radiograph 802. Second radiograph 804 can include a second radiograph pixel 814 at the same x,y position as the first radiograph pixel 812, but located in the second radiograph 804. Similarly, third radiograph 806 can include a third radiograph pixel 816 at the same x,y position as the first radiograph pixel 812 and the second radiograph pixel 814, but located in the third radiograph 806. Finally, fourth radiograph 808 can include a fourth radiograph pixel 818 at the same x,y position as the first radiograph pixel 812, the second radiograph pixel 814, and the third radiograph pixel 816, but located in the fourth radiograph 808. In some embodiments, the first radiograph 802, the second radiograph 804, the third radiograph 806, and the fourth radiograph 808 can be replaced with a single representative radiograph 820. The single representative radiograph 820 can include one or more down-sampled pixels such as positional representative pixel 822. Positional representative pixel 822 can be an average of pixel values at its same x,y position but in consecutive radiographs, for example. For example, the positional representative pixel 822 value can be an average of the first radiograph pixel 812 value, the second radiograph pixel 814 value, the third radiograph pixel 816 value, and the fourth radiograph pixel 818 value since these pixels are all in the same x,y position in their respective radiographs.

In some embodiments, one or more pixels in the representative image generated by inter-radiograph down-sampling are down-sampled pixels. For example, while only one positional representative pixel 822 is shown for illustrative purposes, the representative image 820 can include many more (including all) down-sampled pixels. In some embodiments, inter-radiograph down-sampling reduces the number of total radiograph pixels by 64 times where 4 consecutive radiographs are inter-radiograph down-sampled.

In some embodiments, the one or more down-sampled radiographs can be generated by reducing a reconstruction image resolution. In some embodiments, reducing the reconstruction image can include reducing the reconstruction image to correspond to the one or more down-sampled projection images. In some embodiments, the reconstruction resolution of the volumetric reconstructed image is reduced by the same factor along each dimension as the one or more down-sampled projection images. In some embodiments, the reconstruction resolution is reduced by the same factor along x,y,z axes to match the resolution of the one or more down-sampled projection images. In some embodiments, the number of operations performed by the Filtered Back Projection (FBP) reconstruction algorithm is proportional to the number of voxels in the volume times the number of input projections.

In some embodiments, radiographs from the CT scan be down-sampled using a single down-sampling technique, or any combination of down-sampling techniques such as block sampling, inter-radiograph down-sampling, and/or reconstruction resolution sampling.

As an example, combining inter-radiograph sampling of 4 radiographs and reconstruction resolution sampling by 4 in each dimension (x,y,z), the reconstruction time can be theoretically speed up by 4*4*4*4=256 times, for example. In some embodiments, the sped up reconstruction time allows more reconstructions and estimations of more transfer functions.

In some embodiments, automatically determining photon-count to penetrated depth function for a CT reconstruction can include performing one or more test CT reconstructions on one or more radiographs, each test CT reconstruction using a different test transfer function, to provide one more test reconstructions.

In some embodiments, the computer-implemented method can select a transfer function from a multi-parameter function family t(a, b, c, d, . . . ). In some embodiments, the real transfer function t can include a polynomial of theoretical transfer function:

$$u = 1 - \frac{\ln I}{\ln I_0}:$$

In some embodiments, each test transfer function can include one or more coefficients $t(a, b, c, d, \ldots) = au + bu^2 + cu^3 + du^4 + \ldots$, where $a + b + c + d + \ldots = 1$. In some embodiments, the best parameters for the transfer function can be determined using any non-linear optimization technique known in the art. One example of a non-linear optimization technique known in the art can include, for example, the Levenberg-Marquardt Method described in NUMERICAL RECIPES IN C: THE ART OF SCIENTIFIC COMPUTING, by William H. Press, Brian P. Flannery, Saul A. Teukolsky, and William Vetterling, Cambridge University Press; $2^{nd}$ Edition, (C) 1988-1992, which is hereby incorporated by reference in its entirety. In some embodiments, the one or more test CT reconstructions can be performed using parameters for the transfer function by trying all values of parameters in certain domain and with certain step, e.g.

$a \in [0, 0.05, 0.1, \ldots 1]$,
$b \in [-6, -5.75, -5.5, \ldots 6]$,
$c \in [-12, -11, -10, \ldots 12]$,
$d = 1 - a - b - c$ In some embodiments, upon defining the one or more numeric parameters such as $a, b, c, d, \ldots$, the computer-implemented method reconstructs a volumetric image based on the transfer function $t(a, b, c, d, \ldots)$ to generate one or more test CT reconstructions. In some embodiments, the computer-implemented method can perform the test CT reconstructions. In some embodiments, the test CT reconstructions can be generated by another external process. In some embodiments, a test CT reconstruction is performed for each test transfer function using one or more radiographs produced by CT scanning. In some embodiments, a test CT reconstruction is performed for each test transfer function on one or more down-sampled radiographs. In some embodiments, multiple test CT reconstructions are performed.

In some embodiments, the computer-implemented method can perform one or more test CT reconstructions using any CT reconstruction technique known in the art. In some embodiments, the computer-implemented method can perform test CT reconstructions. In some embodiments, the computer-implemented method can perform conventional CT reconstruction, which can include conventional filtering and conventional back-projection. One type of conventional CT reconstruction algorithm can be the filtered back projection algorithm as described in the *Principles of Computerized Tomographic Imaging* publication. Conventional CT reconstruction is also described in Held, Devin, *Analysis of 3D Cone-Beam CT Image Reconstruction Performance on a FPGA* (2016). Electronic Thesis and Dissertation Repository, 4349, the entirety of which is hereby incorporated by reference. The conventional CT reconstruction algorithm can be referred to as the Feldkamp Reconstruction Algorithm, and is described in U.S. Pat. No. 5,375,156A to Kuo-Petravic et al., issued Dec. 20, 1994, the entirety of which is hereby incorporated by reference. Other types of CT reconstruction algorithms known in the art can also be used.

In some embodiments, the computer-implemented method can perform conventional filtering of the one or more radiographs received. In some embodiments, the one or more radiographs can be down-sampled radiographs. Filtering conventionally involves applying a filtering function such as a ramp function or other type of filtering function known in the art to each row of the radiograph. Filtering is known in the art. For example, one or more filtering functions are described in FILTERING IN SPECT IMAGE RECONSTRUCTION, by Maria E. Lyra and Agapi Ploussi, Article in International Journal of Biomedical Imaging, Volume 2011, Article ID 693795, June 2011, which is hereby incorporated by reference in its entirety. In some embodiments filtering can include applying a filter function to the one or more radiograph rows to provide one or more filtered rows. Any type of CT reconstruction filtering function known in the art can be applied. In some embodiments, applying a filtering function can include convolving each row of the radiograph with the filter function to provide a filtered radiograph. In some embodiments, for example, a ramp filtering function can be applied. Any other filter known in the art can be applied in some embodiments, for example. In some embodiments, filtering is done per each row of the radiograph. In some embodiments, filtering is performed on the entire radiograph at once.

In some embodiments, the computer-implemented method can back-project one or more filtered radiographs using conventional back projection techniques known in the art. In some embodiments, the filtered radiographs can be filtered down-sampled radiographs. Back projection is conventionally known, and can include, in some embodiments, smearing back the one or more filtered radiographs on to the reconstruction volume. For example, in some embodiments, the smearing back is along the same rays joining in x-ray source position to hit detector pixels.

As an example, conventional back-projection can include the following steps. For each voxel of the volume being reconstructed, the computer-implemented method can determine a line that passes via the center of the voxel and the x-ray source point, considering that the x-ray source point changes location relative to the object with the rotation of the rotation table. The computer-implemented method can find a detector point where the line hits the detector. The computer-implemented method can take the value of the filtered image from this detector location and add it to the current voxel with an appropriate weight. The computer-implemented method can repeat the steps for all voxels and all projections.

For example, back-projecting for a cone-beam x-ray source is conventionally known as follows, which is back projecting a value that is bilinearly interpolated from a grid of $Q_\beta(p,\xi)$:

$$g(t,s,z) = \int_0^{2\pi} (D^2_{SO}/(D_{SO}-s)^2) Q_\beta(D_{SO}t/(D_{SO}-s)), (D_{SO}z/(D_{SO}-s))) d\beta$$

$$p = p'D_{SO}/D_{SO} + D_{DE}$$

$$\xi = \xi'D_{SO}/D_{SO} + D_{DE}$$

where $(t,s,z)$ is the original coordinate system, $D_{SO}$ is the source to rotation axis distance, $D_{DE}$ is the rotation axis-to-detector distance, so the sum $D_{SO} + D_{DE}$ is the distance from the source to the detector, and $\beta$ is the angular differential change.

Other techniques for performing filtering and back projection known in the art can also be used by the computer-implemented method. In this manner, several test CT reconstructions can be generated.

In some embodiments, the computer-implemented method can determine a real transfer function from the one or more test CT reconstructions. In some embodiments, determining the real transfer function can include determining a quality of the one or more test reconstructions. In some embodiments, determining the real transfer function can include determining a highest quality test reconstruction from the one or more test reconstructions. In some embodiments, determining the quality of a particular test reconstruction of the one or more test reconstructions can include determining a density histogram of voxel values in the particular test reconstruction.

In some embodiments, the density histogram can include determining a frequency distribution of all voxel values within the volumetric density file.

In some embodiments, the histogram can provide a frequency distribution of air and material densities in a reconstruction volume. For example, in some embodiments, the reconstruction volume can be a test CT reconstruction volume. In some embodiments, the reconstruction volume can be received by the computer-implemented system. In some embodiments, the reconstruction volume can be a volumetric density file that contains voxels having density information of one or more materials and surrounding air from a CT scan. The number of voxels at a particular density value can represent the amount of the material/air having that particular density.

Figure 9:
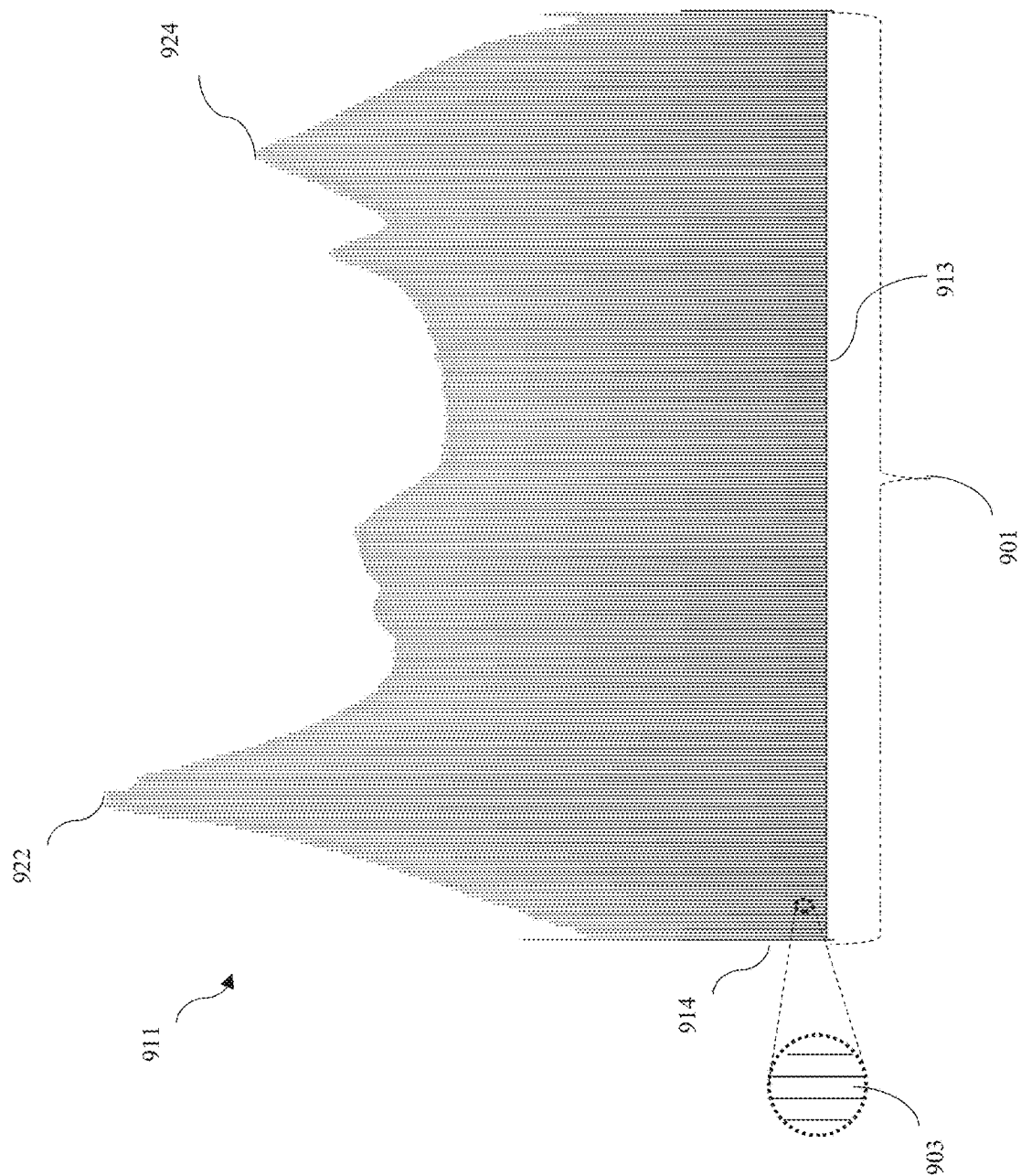
FIG. 9 illustrates an example of a histogram in some embodiments.

As illustrated in the histogram 911 of FIG. 9, in some embodiments, the computer-implemented method can generate a density frequency distribution of the volumetric density file. In some embodiments, the volumetric density file can be that of a test CT reconstruction. In some embodiments, the volumetric density file can be of a final CT reconstruction. The histogram 911 is shown for illustrative purposes and includes an x-axis 913 of density values and the y-axis 914 of the number of voxels (voxel counts), for example. All histograms illustrating the density frequency distribution herein include an x-axis of density values and a y-axis of the number of voxels (voxel counts). In some embodiments, the computer-implemented method can generate a normalized scan density range 901 for the volumetric density file. For example, in some embodiments, the computer-implemented method can generate the normalized scan density range 901 to be between 0.0 and 1.0. The computer-implemented method can subdivide the normalized scan density range into one or more scan density subranges 903 (scan density subrange 903 is shown among multiple scan density subranges in a magnified view). For example, the computer-implemented method can subdivide the normalized scan density range 901 of 0.0 and 1.0 into multiple scan density subranges 903. In some embodiments, each subrange can be numbered starting from 1 to the total number of subranges in the scan density range 901. In some embodiments, the number of scan density subranges 903 can be 500, for example. In some embodiments, more or fewer scan density subranges 903 are possible. For each voxel, the computer-implemented method normalizes the density value of the voxel to fall within the normalized scan density range 901. The computer-implemented method compares the normalized density of the voxel with the one or more scan density subranges 903 and increments the voxel count for the scan density subrange 903 within which the normalized voxel density value falls. The computer-implemented method loads the next voxel from the volumetric density file and repeats the process for every voxel in the volumetric density file to determine the total voxel count for each of the scan density subranges 903. In some embodiments, the computer-implemented method takes a logarithm of the voxel counts for each scan density subrange 903. The subrange can also be referred to as a "bin", with the subrange number corresponding to a bin number. The computer-implemented method in this manner can generate the density frequency distribution which is depicted as histogram 911 for illustrative purposes for one or more of the test CT reconstructions.

In some embodiments, determining the quality of the particular test reconstruction of the one or more test reconstructions can include determining a precise location and a height of one or more peaks in the density histogram of the particular test reconstruction. In some embodiments, the one or more peaks can include a highest peak. In some embodiments, the highest peak corresponds to air density. In some embodiments, the one or more peaks can include a second highest peak. In some embodiments, the second highest peak corresponds to a main material density.

FIG. 9 illustrates a first highest peak 922 and a second highest peak 924. In some embodiments, the first highest peak 922 can correspond to air density and the second highest peak 924 can correspond to a main material density.

In some embodiments, determining the precise location and height of the one or more peaks can include determining a precise density value and a precise peak height at the density value for the peak. In some embodiments, the precise location can be a density value that is a floating point density value. In some embodiments, the precise location density value can be determined from a bin number of the peak. The bin number of the peak can be an integer value. In some embodiments the integer valued location of a peak is its bin (subrange) number.

In some embodiments, the computer-implemented method can determine a peak bin number for a peak. The computer-implemented method can determine a local maximum peak bin and a pair of lower density bins to the immediate left of the peak bin in the histogram (i.e. having density values less than the peak bin) and a pair of higher density bins to the immediate right of the peak bin in the histogram (i.e. having density values greater than the peak bin). The computer-implemented method can determine a best parabola approximating the five points of the peak bin values. The five points can include the local maximum peak bin, the pair of lower density bins to the left of the peak bin and the pair of higher density bins to the right of the peak bin. In some embodiments, the computer-implemented method can determine a location of the parabola maximum and its value as the height of the peak and it's position as the location of the peak. In some embodiments, determining the location and height of the one or more peaks can include determining the location and height of the highest peak and the second highest peak.

Figure 10:
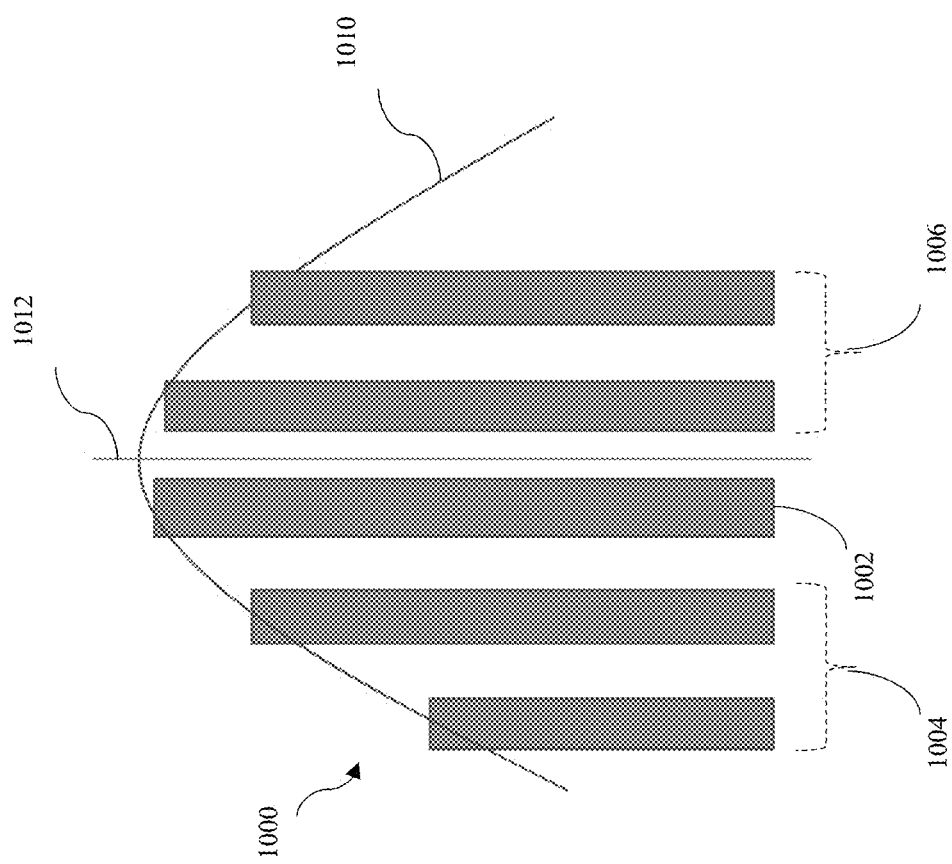
FIG. 10 illustrates an example of determining the location and height of one or more peaks in some embodiments.

FIG. 10 illustrates an example of determining the location and height of one or more peaks in some embodiments. The figure shows a portion of a histogram (frequency distribution) 1000 with five bins with a peak bin 1002. Peak bin 1002 can be either the highest peak or the second highest peak. The same process can be applied to both the highest peak and the second highest peak to determine their exact position and height. As can be seen in the figure, the computer-implemented method determines a pair of lower density bins 1004 adjacent to left of the peak bin 1002 in the histogram. The pair of lower density bins 1004 have a density values less than the peak bin 1002. The computer-implemented also determines a pair of higher density bins 1006 to right of the peak bin 1002 in the histogram. The pair of higher density bins 1006 have density values higher than the peak bin 1002. The computer-implemented method can determine a best fit parabola 1010 through the pair of lower density bins 1004, the peak bin 1002, and the pair of higher density bins 1006. The computer-implemented method can determine the precise location and height of the peak 1012 from the highest point of the best fit parabola 1010.

Figure 11:
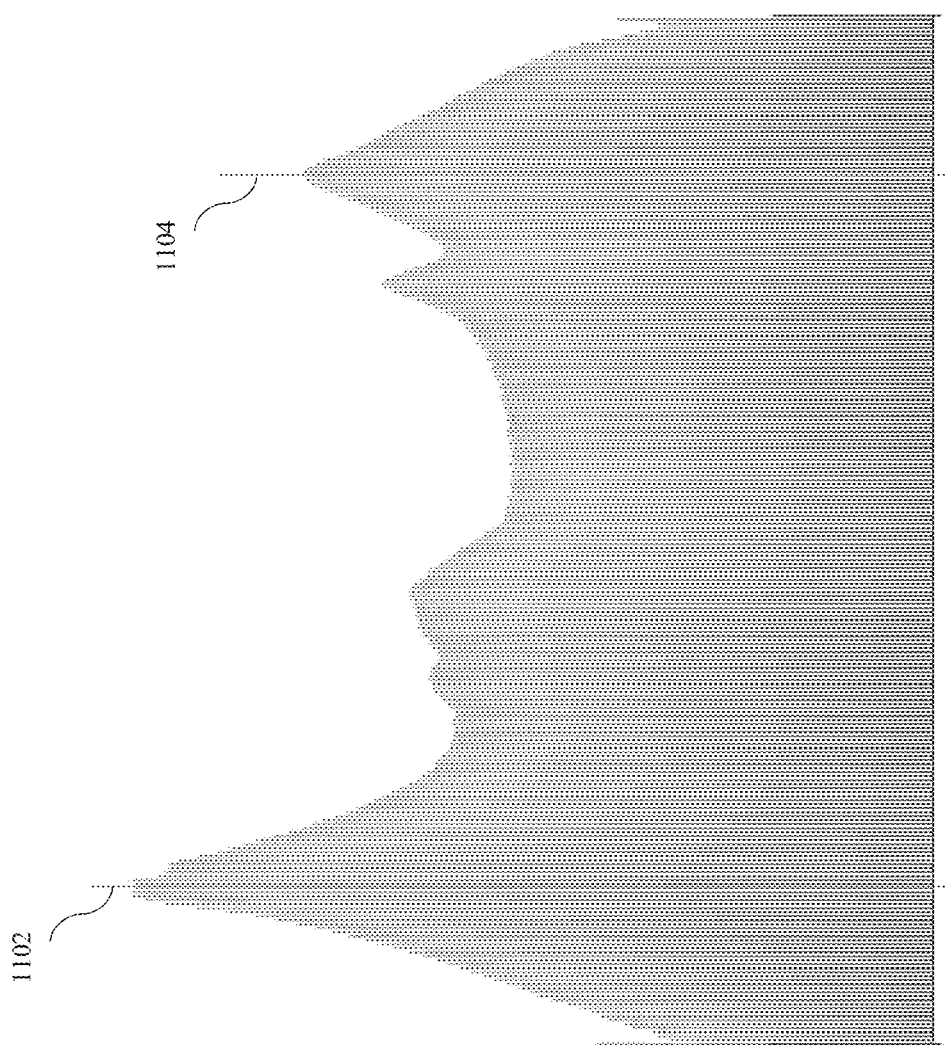
FIG. 11 illustrates an example of a histogram in some embodiments with a highest peak and a second highest peak in some embodiments.

As illustrated in FIG. 11, the computer-implemented method can determine the exact location and height of the highest peak 1102 and the second highest peak 1104.

In some embodiments, determining the quality of the one or more test reconstructions can include determining, for a particular test reconstruction, the quality of the reconstruction, q, as follows:

$$q = h_m(d_m - d_a)/(d_{max} - d_{min})$$

In some embodiments, the histogram can include a minimum density $d_{min}$ to maximum density $d_{max}$ and given air peak location $d_a$ and main material location $d_m$ and height $h_m$. In some embodiments, the highest quality test reconstruction is the one with the greatest q value. In some embodiments, the quality is determined for at least one of the one or more test reconstructions. In some embodiments, the quality is accordingly determined for each test transfer function, each test transfer function having parameter values a, b, c, d, . . . . In some embodiments, the computer-implemented method determines the quality as a non-linear function of the parameters q(a, b, c, d, . . . ). In some embodiments, the quality is determined for all of the one or more test reconstructions. In some embodiments, the computer-implemented method determines the best quality (highest q) from the test reconstructions to determine the best test reconstruction. In some embodiments, the computer-implemented method selects the transfer function corresponding to the best test reconstruction as the real transfer function on which to perform final CT reconstruction.

Figure 12:
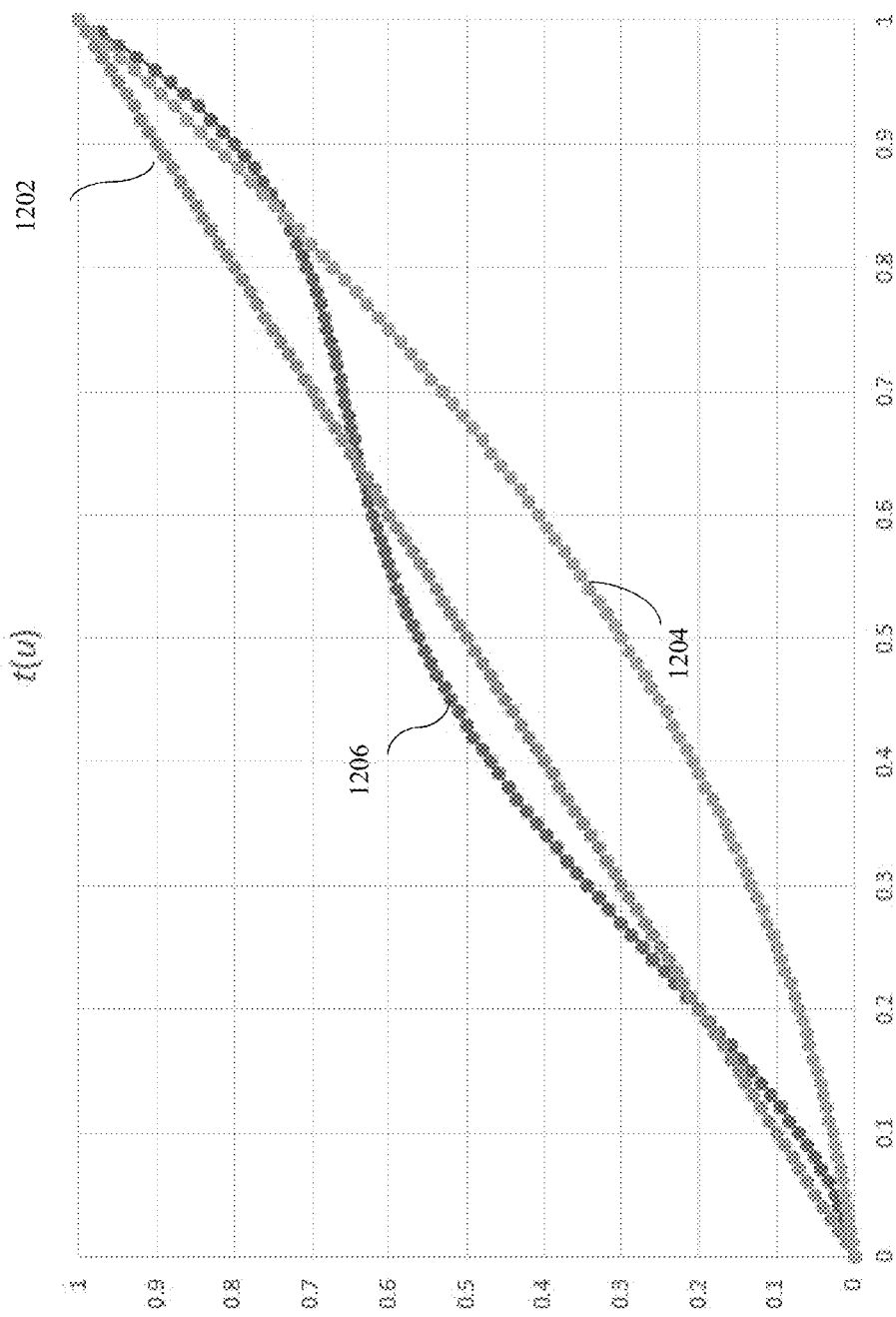
FIG. 12 is a graph showing an example various transfer functions in some embodiments.

FIG. 12 shows one example of transfer functions such as a theoretical transfer function 1202, where t=u, a manually set transfer function 1204, where $t=0.2u+0.8u^2$, and a real transfer function 1206, where $t=0.25u+5.75u^2-11u^3+6u^4$. These example transfer functions are shown for illustrative purposes only, and the disclosure is not limited to or by these example transfer functions. Other transfer functions are possible.

Figure 13:
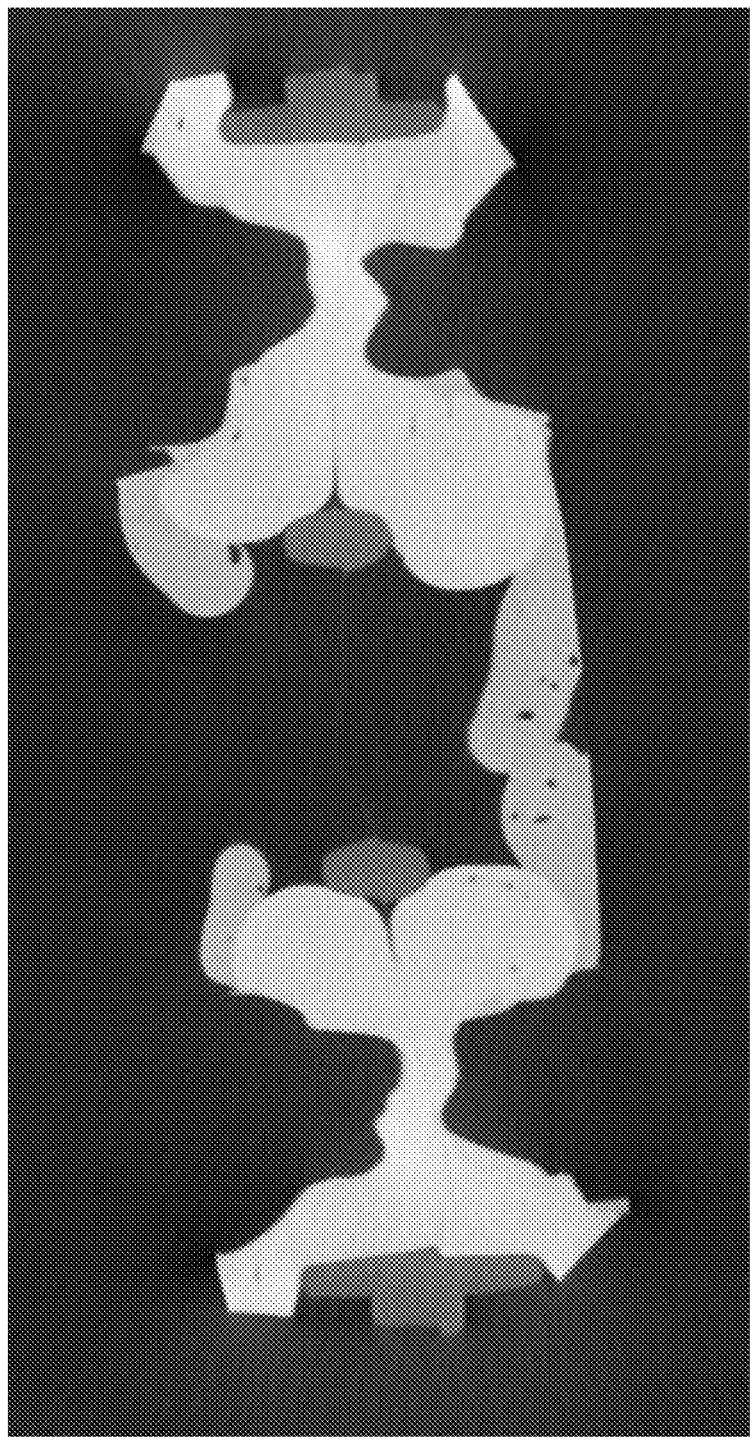
FIG. 13 shows an example of a final CT reconstruction performed using a real transfer function in some embodiments.

FIG. 13 shows an example of a final CT reconstruction with reduced or eliminated stokes and with consistent density for the same material in the reconstructed volume. The final CT reconstruction is for illustrative purposes only, and the disclosure is not limited to or by the example illustrated in FIG. 13.

In some embodiments, once the computer-implemented method determines the real transfer function, the computer-implemented method can perform a final CT reconstruction using the real transfer function and the radiographs from CT scanning (not down-sampled radiographs). In some embodiments, the computer-implemented method provide the real transfer function to another process that can perform the final CT reconstruction.

In some embodiments, the entire process can be automated—without user input. For example, the computer-implemented method can receive one or more radiographs, automatically perform optional down-sampling, automatically generate one or more test reconstructions, automatically determine the best test reconstruction, automatically determine the real transfer function, and optionally automatically perform final CT reconstruction using the real transfer function.

Figure 14:
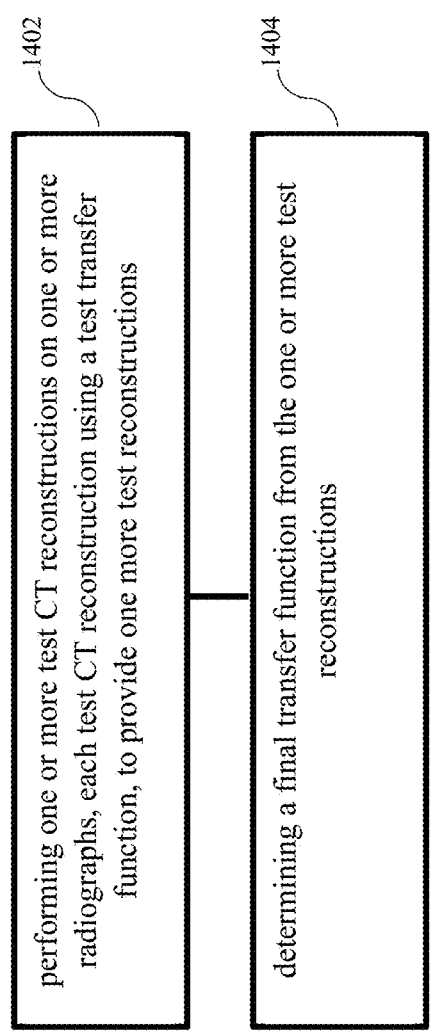
FIG. 14 illustrates a flow diagram in some embodiments of a computer-implemented method of automatically determining photon-count to penetrated depth function for a CT reconstruction.

FIG. 14 illustrates a flow diagram in some embodiments of a computer-implemented method of automatically determining photon-count to penetrated depth function for a CT reconstruction. The computer-implemented method can include performing one or more test CT reconstructions on one or more radiographs, each test CT reconstruction using a test transfer function, to provide one more test reconstructions at 1402 and determining a final transfer function from the one or more test reconstructions at 1404. In some embodiments, the one or more radiographs comprise one or more down-sampled radiographs. In some embodiments, the one or more down-sampled radiographs are generated prior to generating one or more test CT reconstructions. In some embodiments, the one or more down-sampled radiographs are generated by replacing a block of pixels in each of one or more CT scanner radiographs with a single representative pixel. In some embodiments, one or more down-sampled radiographs are generated by replacing one or more consecutive CT scanner radiographs with a single representative radiograph. In some embodiments, determining the final transfer function comprises determining a quality of the one or more test reconstructions. In some embodiments, determining the quality of a particular test reconstruction of the one or more test reconstructions comprises determining a highest peak location and height and a second highest peak location and height in a density histogram of the particular test reconstruction.

Figure 15:
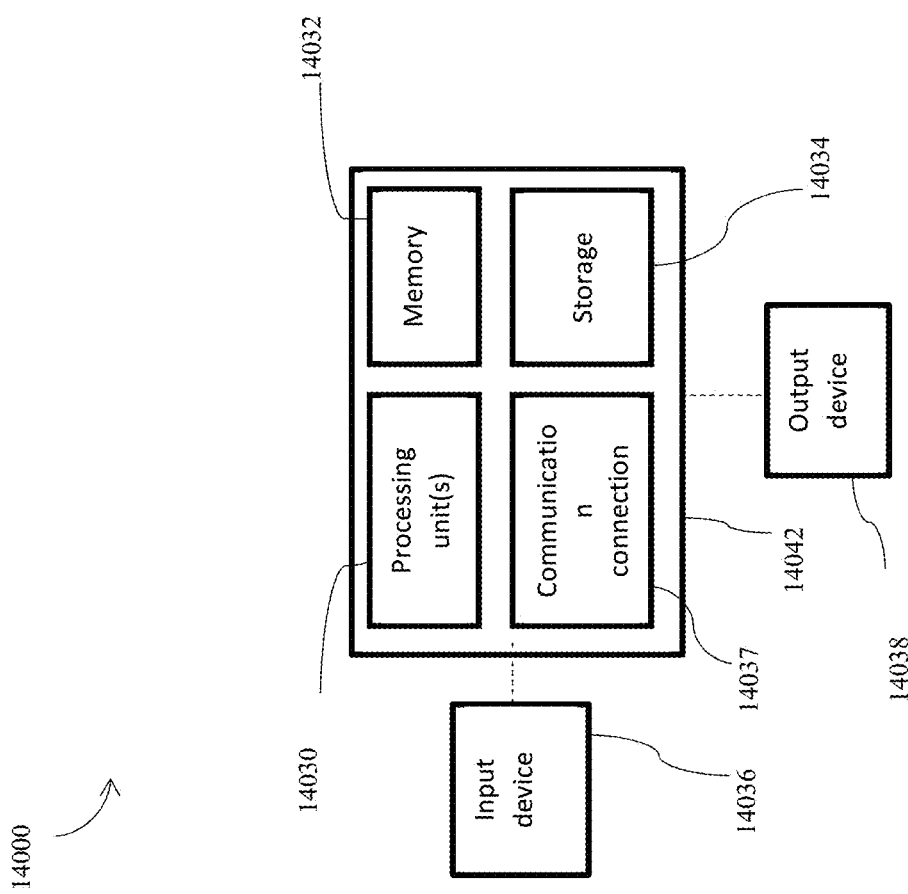
FIG. 15 illustrates a processing system in some embodiments.

FIG. 15 illustrates a processing system 14000 in some embodiments. The system 14000 can include a processor 14030, computer-readable storage medium 14034 having instructions executable by the processor to perform one or more steps described in the present disclosure.

One or more advantages of one or more features can include, for example, reduction or elimination of undesirable artifacts in the 3D representation of the object scanned, particularly for scanned objects made of different materials. One or more advantages of one or more features can include allowing reconstruction without requiring precise measurements of various path lengths. One or more advantages of one or more features can include, for example, reconstruction of an object made of different. One or more advantages of one or more features can include, for example, reconstruction without developing a calibration object. One or more advantages of one or more features can include, for example, automatic determination of a real transfer function. One or more advantages of one or more features can include, for example, fast generation of test reconstructions using down-sampled radiographs. One or more advantages of one or more features can include, for example, improved reconstruction accuracy. One or more advantages of one or more features can include, for example, reduction or elimination of artifacts such as stokes and/or other artifacts One or more advantages of one or more features can include, for example, reduction or elimination of different density values for the same material in the reconstruction.

One or more of the features disclosed herein can be performed and/or attained automatically, without manual or user intervention. One or more of the features disclosed herein can be performed by a computer-implemented method. The features—including but not limited to any methods and systems—disclosed may be implemented in computing systems. For example, the computing environment 14042 used to perform these functions can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only examples and should not be taken as limiting the scope of the disclosure.

What is claimed is:

1. A computer-implemented method of automatically determining photon-count to penetrated depth function for a CT reconstruction, comprising:
    performing one or more test CT reconstructions on one or more radiographs, each test CT reconstruction using a test transfer function, to provide one more test reconstructions; and
    determining a final transfer function from the one or more test reconstructions.

2. The method of claim 1, wherein the one or more radiographs comprise one or more down-sampled radiographs.

3. The method of claim 2, wherein the one or more down-sampled radiographs are generated prior to generating one or more test CT reconstructions.

4. The method of claim 2, wherein the one or more down-sampled radiographs are generated by replacing a block of pixels in each of one or more CT scanner radiographs with a single representative pixel.

5. The method of claim 2, wherein the one or more down-sampled radiographs are generated by replacing one or more consecutive CT scanner radiographs with a single representative radiograph.

6. The method of claim 1, wherein determining the final transfer function comprises determining a quality of the one or more test reconstructions.

7. The method of claim 6, wherein determining the quality of a particular test reconstruction of the one or more test reconstructions comprises determining a highest peak location and height and a second highest peak location and height in a density histogram of the particular test reconstruction.

8. A system to automatically determine a photon-count to penetrated depth function for a CT reconstruction, the system comprising:
    a processor; and
    a non-transitory computer-readable storage medium comprising instructions executable by the processor to perform steps comprising:
    performing one or more test CT reconstructions on one or more radiographs, each test CT reconstruction using a test transfer function, to provide one more test reconstructions;
    determining a final transfer function from the one or more test reconstructions.

9. The system of claim 8, wherein the one or more radiographs comprise one or more down-sampled radiographs.

10. The system of claim 9, wherein the one or more down-sampled radiographs are generated prior to generating one or more test CT reconstructions.

11. The system of claim 9, wherein the one or more down-sampled radiographs are generated by replacing a block of pixels in each of one or more CT scanner radiographs with a single representative pixel.

12. The system of claim 10, wherein the one or more down-sampled radiographs are generated by replacing one or more consecutive CT scanner radiographs with a single representative radiograph.

13. The system of claim 8, wherein determining the final transfer function comprises determining a quality of the one or more test reconstructions.

14. The system of claim 13, wherein determining the quality of a particular test reconstruction of the one or more test reconstructions comprises determining a highest peak location and height and a second highest peak location and height in a density histogram of the particular test reconstruction.

15. A non-transitory computer readable medium storing executable computer program instructions to automatically determine a photon-count to penetrated depth function for a CT reconstruction, the computer program instructions comprising instructions for:
    performing one or more test CT reconstructions on one or more radiographs, each test CT reconstruction using a test transfer function, to provide one more test reconstructions;
    determining a final transfer function from the one or more test reconstructions.

16. The medium of claim 15, wherein the one or more radiographs comprise one or more down-sampled radiographs.

17. The medium of claim 16, wherein the one or more down-sampled radiographs are generated prior to generating one or more test CT reconstructions.

18. The medium of claim 16, wherein the one or more down-sampled radiographs are generated by replacing one or more consecutive CT scanner radiographs with a single representative radiograph.

19. The medium of claim 15, wherein determining the final transfer function comprises determining a quality of the one or more test reconstructions.

20. The medium of claim 19, wherein determining the quality of a particular test reconstruction of the one or more test reconstructions comprises determining a highest peak location and height and a second highest peak location and height in a density histogram of the particular test reconstruction.

* * * * *